United States Patent [19]
Nychka et al.

[11] 4,088,704
[45] May 9, 1978

[54] PRODUCTION OF FLUOROCARBONS EMPLOYING TWO CATALYST ZONES

[75] Inventors: Henry R. Nychka, E. Aurora; Richard E. Eibeck, Orchard Park, both of N.Y.

[73] Assignee: Allied Chemical Corporation, Morris Township, N.J.

[21] Appl. No.: 761,161

[22] Filed: Jan. 21, 1977

[51] Int. Cl.$^2$ ............................................. C07C 17/10
[52] U.S. Cl. .................... 260/653; 260/653.7; 260/653.8
[58] Field of Search .................. 260/653, 653.7, 653.8

[56] References Cited
U.S. PATENT DOCUMENTS

| | | | |
|---|---|---|---|
| 3,476,817 | 11/1969 | Vecchio | 260/653.7 |
| 3,652,692 | 3/1972 | Vecchio et al. | 260/653.7 |
| 3,793,229 | 2/1974 | Groppelli et al. | 260/653.7 |

Primary Examiner—C. Davis
Attorney, Agent, or Firm—Alan M. Doernberg

[57] ABSTRACT

Highly chlorinated hydrocarbons having one to three carbons such as $CCl_4$, $C_2Cl_6$ and $C_3Cl_8$ are reacted with HF in the presence of a fluorination catalyst such as gamma aluminum fluoride. The effluent is reacted with unhalogenated or underhalogenated hydrocarbons having 1 to 3 carbons, such as $CH_4$, $CH_3Cl$, $C_2H_5Cl$, $C_2H_6$, $CH_2=CHCl$ and $CFCl=CCl_2$, and $O_2$ in the presence of an oxychlorination catalyst, such as cupric chloride with alkali halide or alkaline earth halide promoters on alpha aluminum fluoride. Fluorocarbons having 1 to 3 carbons such as $CCl_2F_2$, $C_2Cl_3F_3$ and $C_2Cl_2F_4$ are separated from the effluent. Preferably, highly chlorinated materials are recycled onto the fluorination catalyst and underhalogenated materials are recycled onto the oxychlorination catalyst.

12 Claims, No Drawings

PRODUCTION OF FLUOROCARBONS EMPLOYING TWO CATALYST ZONES

BACKGROUND OF THE INVENTION

The invention relates to methods of preparing fluorocarbons, and particularly fluorocarbons having 1 to 3 carbons.

Fluorocarbons, carbon compounds with a carbon skeleton and at least one fluorine, are conventionally prepared by beginning with the chlorination of non-halogenated hydrocarbons in a first reactor system. Hydrochloric acid is usually produced by this reaction, and must be disposed of if not reused. Although several oxychlorination systems have been proposed which would consume the hydrochloric acid in forming new chlorinated hydrocarbons, such systems have not been commercially successful. Subsequently, the chlorinated hydrocarbon is fluorinated using either elemental fluorine or HF in the presence of such a catalyst as pentavalent antimony, sometimes producing more hydrochloric acid.

The production of fluorocarbons by a one step oxychlorofluorination, although suggested by British Patent No. 745,818, has not been commercialized.

SUMMARY OF THE INVENTION

The invention includes a process for producing chlorofluorinated hydrocarbons by reacting highly chlorinated hydrocarbons such as carbon tetrachloride, chloroform, perchloroethylene, perchloropropane and mixtures thereof with hydrogen fluoride in the presence of a fluorination catalyst, and reacting the effluent with underhalogenated and unhalogenated hydrocarbons having 1 to 3 carbons and oxygen in the presence of an oxychlorination catalyst. The oxychlorination catalyst should be inert to hydrogen fluoride and, preferably, relatively non-combustionpromoting. Desired fluorocarbons having 1 to 3 carbons are recovered from the effluent.

In preferred forms, highly chlorinated hydrocarbons are recovered from the effluent and recycled onto the fluorination catalyst. Underhalogenated and non-halogenated hydrocarbons are recovered from the effluent and recycled onto the oxychlorinating catalyst.

Preferred fluorination catalyst include the gamma fluoride of aluminum, the fluorides of chromium, nickel, cobalt, thorium and zirconium, and the partially fluorinated oxides of aluminum and chromium. Preferred oxychlorination catalysts include an inert base and a coating of a transition metal chloride such as cupric chloride with one or more alkali or alkaline earth salt promoters.

In preferred forms, the process is carried out in a reaction bed with two catalyst zones, an upstream fluorination catalyst zone and a downstream oxychlorination catalyst zone. The hydrogen fluoride and perchlorinated hydrocarbons are introduced at the upstream end. Non-halogenated and underhalogenated hydrocarbons are introduced adjacent the interface between the two catalyst zones onto the oxychlorination catalyst. Oxygen may be introduced at the upstream end or adjacent the interface. The effluent is separated, as by distillation, into (1) one or more perchlorinated hydrocarbon fractions which are recycled to the upstream end, (2) one or more underhalogenated or non-halogenated hydrocarbon fractions which are recycled onto the oxychlorination catalyst zone, and (3) one or more fluorocarbon product fractions.

DETAILED DESCRIPTION OF THE INVENTION

The present process can produce one, two or three carbon fluorocarbons. Usually the process would operate at a single carbon level, with all carbon-containing reactants, intermediates and products having the same chain length. Mixtures of carbon chain lengths could be present in one system; however, mixture of carbon chain lengths would multiply the different compounds in each component, including fluorocarbon products, and are not preferred. Most of the following description, which is phrased in terms of ethane derivatives, is equally applicable to methane or propane derivatives, except as specifically noted.

The raw materials for the process include oxygen, HF and non-halogenated or underhalogenated hydrocarbon. Several types of carbon-containing materials are formed as reactants, intermediates and products. They have 1–3 carbons with only H, Cl and/or F thereon. All compounds containing carbon and oxygen are considered "combustion products" and regarded as a generally undesired product of direct oxidation. By non-halogenated hydrocarbon is meant methane, ethane or propane. By underhalogenated hydrocarbon is meant, first, any substituted hydrocarbon with at least one remaining hydrogen. For purposes of this invention, unsaturated hydrocarbons are also regarded as "underhalogenated" hydrocarbons in that two halogens may still be added to the carbon skeleton by eliminating the double bond. For example, of the unsaturates $CCl_2=CCl_2$ and $CCl_3CCl=CCl_2$ may be regarded as "underhalogenated" hydrocarbons for some purposes. However, they may also be used to dissolve perchlorinated hydrocarbons, or may be chlorinated to perchlorinated hydrocarbons. Perchlorinated hydrocarbons are $CCl_4$, $C_2Cl_6$ and $C_3Cl_8$.

$CHCl_3$, $CCl_2=CCl_2$ and $CCl_3CCl=CCl_2$ shall be called "highly chlorinated" hydrocarbons and, as desired, may be grouped with the underhalogenated hydrocarbons for some purposes and with the perchlorinated hydrocarbons for other purposes.

Compounds containing less fluorines than the desired product or products may be regarded as if the fluorines were chlorine. Thus, if the desired products are $C_2Cl_3F_3$ and $CCl_2F_4$, then $C_2Cl_4F_2$ and $C_2Cl_5F$ may be regarded as "perchlorinated" hydrocarbons and, as described below, recycled onto the fluorination catalyst. Similarly $CCl_2F_2$, $CCl_3F$, $C_3Cl_6F_2$, $C_3Cl_7F$ and the like may be regarded as "perchlorinated" if more fluorinated products are desired. $CCl_2=CClF$ and the like may be regarded as "underhalogenated" or "perchlorinated" hydrocarbons as with $CCl_2=CCl_2$ as discussed above. $CCl_2=CClF$ may be chlorinated to $CCl_3CCl_2F$ before or during recycling with the perchlorinated hydrocarbon, or introduced as an underhalogenated hydrocarbon into the oxychlorination zone. $C_2HCl_4F$ and the like are regarded as underhalogenated.

It will be appreciated that formulas such as $C_2Cl_4F_2$ and $C_2HCl_3F_2$ actually each describe two or more structural isomers, and formulas such as $CClF=CClF$ and $CCl_3CF=CClF$ actually describe cis-trans isomers. For purposes of this process, structural and cis-trans isomerism may be generally disregarded, and the formulas may indicate any one isomer or mixture of isomers. It will be appreciated, however, that one isomer may be preferentially formed or reacted in the process over the other or others so that equal or random mixtures of isomers may not necessarily be found.

FLUORINATION ZONE

The reaction occurring in the fluorination zone is the fluorination of "perchlorinated" and/or "highly chlorinated" hydrocarbons, as defined above, with HF in the presence of a fluorination catalyst. As discussed above, compounds such as $C_2Cl_5F$ may be considered "perchlorinated" hydrocarbons if more fluorination is desired. Compounds such as $CCl_2=CCl_2$ may also, as discussed above and illustrated in the Examples, be regarded as "perchlorinated" if they are to be used as a carrier for perchlorinated hydrocarbons such as $C_2Cl_6$. If $Cl_2$ is introduced therewith, compounds such as $CCl_2=CCl_2$ may be regarded as "perchlorinated" for the additional reason that the $Cl_2$ can be added in situ across the double bond to produce perchlorinated hydrocarbons.

Preferred highly chlorinated hydrocarbons are the perchlorinated hydrocarbons $CCl_4$, $C_2Cl_6$ and $C_3Cl_8$. Other highly chlorinated hydrocarbons with one or two hydrogens such as $CHCl_3$ may be fed into the fluorination zone if fluorcarbon products with one or two hydrogens are desired. $CHCl_3$ is generally suitable since it can be fluorinated by using such catalysts as gamma aluminum fluoride. $C_2HCl_5$ and $C_3HCl_7$ are generally less preferred since they are not easily fluorinated by using such catalysts as gamma aluminum fluoride. The two hydrogen compounds $CH_2Cl_2$, $C_2H_2Cl_4$ and $C_3H_2Cl_6$ are even less preferred as highly chlorinated hydrocarbons, and are preferably treated as underhalogenated. Such materials can, however, be used with stronger fluorination catalysts such as pentavalent antimony. Of course, as discussed above, $CHCl_2F$ and the like may be regarded as highly chlorinated if more fluorination is desired. If only perhalogenated fluorocarbon products are desired, only perchlorinated compounds such as $C_2Cl_6$ or $C_2Cl_5F$ would normally be introduced into the fluorination zone.

The fluorination catalyst may be any catalyst with fluorination activity for the reaction of HF with "perchlorinated" or highly chlorinated hydrocarbons. A broad range of such catalysts are well known in the art and, any of them may be used as the fluorination catalyst. Pentavalent antimony catalysts, as are known containing fluoride ions, chloride ions or both such as $SbCl_2F_3$ and $SbF_5$, may be used. Other partial or complete fluorides of various transition metals are known to catalyze fluorination and include, by way of preferred examples, the fluorides of nickel, cobalt, thorium and zirconium. The fluoride of chromium and the ordinary gamma fluoride of aluminum are more preferred. These latter compounds may be cheaply replaced by the products of partial fluorination of chromium oxide or alumina which are mixtures of the preferred fluorides and unreactive oxides.

The product or effluent from the fluorination catalyst will contain fluorocarbon products, hydrochloric acid by-product and unreacted hydrogen fluoride. Much of the "perchlorinated" hydrocarbon such as $C_2Cl_6$ would be reacted in the fluorination zone and not found in the effluent, but other materials such as $C_2Cl_4$, $C_2Cl_5F$ and the like, which might in particular forms be regarded as "perchlorinated" hydrocarbons, would be present in the effluent. If oxygen is fed into the fluorination zone, it will be present in the effluent.

As discussed below, non-halogenated and "underhalogenated" hydrocarbons are not normally present in the fluorination zone to avoid combustion. Furthermore, waste of the $C_2Cl_6$ reactant by the following side reactions is avoided:

$$C_2Cl_6 \rightarrow C_2Cl_4 + Cl_2$$

$$Cl_2 + C_2H_6 \rightarrow C_2H_5Cl + HCl$$

The occurrence of this side-reaction is shown in Example 13.

The reaction parameters in the fluorination zone are not themselves novel. For many reactants and fluorination catalysts a temperature range of about 250° to about 500° C is preferred, as is a contact time of between about 0.1 sec to about 30 sec. The preferred molar ratio of HF to chlorinated and/or highly chlorinated hydrocarbons will vary, but is generally between about 1.0 to 2.0 moles of HF per carbon-chlorine bond.

OXYCHLORINATION ZONE

The entire effluent from the fluorination zone is fed into the oxychlorination zone. Non-halogenated hydrocarbons and/or "underhalogenated" hydrocarbons, as defined above, are also fed into the oxychlorination zone as a carbon source. If oxygen was not fed in the fluorination zone, then it is fed into the oxychlorination zone.

The carbon source may be any hydrocarbon or halogenated hydrocarbon with less halogens than the desired product. For example the hydrocarbons ethane or ethylene may be used in a two carbon process, or ethyl chloride, $C_2H_5Cl$ may be used. Such low-chlorine compounds are preferable as the initial feed, and they may be used as the outside feed (in addition to the recycle) as the process proceeds. More halogenated compounds such as $C_2H_2Cl_4$, $CHCl=CHCl$ or even $CHCl=Cl_2$ may be used as "underhalogenated" hydrocarbons, and are preferably fed as a recycle as discussed below. If highly chlorinated compounds such as $C_2HCl_5$ and $C_2HCl_4F$ are not fed into the fluorination zone, because monohydrogen fluorocarbon products are not desired as discussed above, they may be regarded as "underhalogenated" hydrocarbons and fed into the oxychlorination zone, usually as a recycle.

Many oxychlorination catalysts and materials found in oxychlorination catalysts are less preferred because they promote combustion of the non-halogenated or "underhalogenated" hydrocarbon in the presence of oxygen. Although some combustion may occur even with the preferred catalysts, it has been found that this combustion can be minimized. A strong correlation has been seen and is believed to exist generally between catalysts which promote fluorination and catalysts which promote combustion. Thus, catalysts with low fluorination activity are preferred as oxychlorination catalysts because they are non-combustion-promoting.

Thus, the gamma form of aluminum fluoride suitable for the fluorination catalyst would be an undesirable component in the oxychlorination catalyst. If such a good combustion promoter were present in any significant quantity in the oxychlorination zone where non-halogenated hydrocarbons are present, a substantial portion of the non-halogenated hydrocarbons might be lost to combustion. Even underhalogenated hydrocarbons such as $C_2H_5Cl$ are somewhat susceptible to combustion. However, small amounts of the fluorination catalyst could migrate to the oxychlorination zone without unacceptable combustion levels.

Of course, in the fluorination zone, no non-halogenated or "underhalogenated" hydrocarbons need be present, as they are introduced further downstream. The "perchlorinated" or "highly chlorinated" hydrocarbons that are present in the fluorination zone are relatively nonreactive with oxygen, even in the presence of combustion-promoting catalysts such as gamma aluminum fluoride.

Oxygen may also be kept out of the fluorination zone, by feeding it adjacent the zone interface, but this may be less desired. As recognized generally in U.S. Pat. No. 3,476,816, oxygen may promote or otherwise improve the fluorination activity of the fluorination catalyst. However, by failing to segregate non-halogenated hydrocarbon from the fluorination catalyst, this prior art causes an unecessary combustion loss in return for the increased fluorination activity.

Preferred oxychlorination catalysts are also inert to attack or deactivation by HF. For example, siliceous materials are dissolved by HF and would be unsuitable.

The preferred oxychlorination catalysts are the "Deacon Catalysts" which are oxides and halides of transition metals having more than one valence state. Illustrative of such metals are Cu, Sn, Ni, Rh, Fe, V, Mn, Co, Pb, Cd, Hg, Pb, Ce and Cr. The preferred metal is Cu. Illustrative suitable catalysts are $CuCl_2$, $Cu_2O$, $CuO$, $FeCl_2$, $FeCl_3$, $FeO$, $Fe_2O_3$, $Cu_2Cl_2$ $Cr_2O_3$, $CrCl_3$, $MnCl_2$, $MnBr_2$, $MnO_2$, $SnCl_2$, $NiBr_2$, $RhCl_3$, $VCl_3$, $CoO_2$, $PbCl_2$, $Cd(NO_3)_2$, $HgBr_2$, $PbCl_2$ and $Ce(NO_3)_3$. Preferred is copper chloride. Mixtures of Deacon catalysts may be employed. Other metal salts may be added to the Deacon catalyst, such as alkali or alkaline earth metal chlorides. These may serve to promote the oxychlorination (Deacon) reaction or inhibit combustion and hydrolysis reactions. Illustrative are the chlorides of Li, Na, K, Rb, La, Th, Ca, Ta and Cs. Although excesses of promoter are not undesirable, molar ratios of from about 0.5:1 to 2:1 of promoter to Deacon catalyst are preferred, and molar ratios about 1:1 are most preferred.

The catalyst is preferably used in combination with a stable, inert metal carrier.

By "stable" is intended to mean that the carrier is dimensionally and physically stable in the sense that when used in a fixed bed reactor, no more than 20% by weight of the carrier crumbles or converts to a powder from its original granular or pelleted form after 500 hours of operation, or when used in a fluidized bed reactor, the carrier does not undergo erosion or agglomeration to the extent that the particle size distribution changes sufficiently to adversely affect the operation of the fluidized bed. Acceptable particle size distributions for fluidized bed reactions are set by standard engineering practice well known to persons skilled in the art. It is also a characteristic of being "stable" for the purpose of this description that the carrier is substantially non-volatile and non-melting at temperatures up to about 550° C.

By "inert" is intended to mean that which is or becomes substantially non-reactive with the organic starting materials, HF, HCl, $Cl_2$ and $O_2$. Some minor reaction with the aforementioned materials can be tolerated provided that such reaction does not adversely affect the oxychlorination reaction or the catalyst life. Alumina ($Al_2O_3$) is not considered to be inert within this definition because it undergoes substantial reaction with HF under oxychlorination conditions. An example of a permissible minor reaction is the formation of small amounts of fluorides and/or oxyfluorides which will not further react with the aforementioned materials. The term "inert" is not intended to exclude catalytically active materials provided such materials satisfy the other requirements for being inert as described above. For example, a material satisfying the requirements for the stable, inert, metal salt carrier as defined herein, may also function as a Deacon catalyst, as defined herein. However, combustion-promoting materials such as most fluorination catalysts are non-preferred. In any event, for the purposes herein, the expression Deacon catalyst supported by a stable, inert, metal salt carrier can refer to a single substance.

A variety of metal salts meet these criteria of being stable and inert including, for example, fluorides, oxyhalides, or oxides and admixtures thereof of Al (the alpha form), Mg, Ca, Ba, V, Sr, Cd, Pb, Cr and Fe, or combinations thereof. Illustrative suitable metal salts are alpha $AlF_3$, $MgF_2$, $CaF_2$, $BaF_2$, $V_2O_3$, $SrF_2$, $NiF_2$, $CdF_2$, $PbO$, $CrF_3$ and $Fe_2O_3$. The preferred anion for the metal salt carriers is fluoride. The preferred cation is aluminum and the preferred support material is $AlF_3$ (alpha form). Depending on the results desired, choice of the stable, inert metal salt support may have a substantial influence on the particular oxychlorination reaction involved.

The metal salt used as the support may be prepared beforehand or formed in situ during the reaction. For example, the Deacon catalyst may be impregnated on alumina (aluminum oxide). Under the particular oxychlorination conditions of the present reactions, including exposure to HF at elevated temperatures, the surface of the alumina is converted to $AlF_3$. The process aspects of this invention employing such catalysts are considered to be part of the invention herein, although this is not a preferred mode of operation. Preferably, the support throughout the oxychlorination reaction comprises at least about 80% by weight of the metal salt and, still preferably, at least about 90% by weight of the metal salt. German Pat. No. 2,114,457 discloses a number of chlorofluorination catalysts including $CuCl_2$ impregnated on a support such as aluminum oxide in which the catalyst loading is between about 1–10 weight percent metal based on the total weight of the catalyst salts and the support material. It is disclosed that during the chlorofluorination reaction the surface of the aluminum oxide is presumed to be converted to $AlF_3$, however, it is believed that the gamma fluoride would be formed, leading to undesired combustion levels.

The preferred support material, alpha $AlF_3$, may be prepared by fluorinating alumina with HF at high temperatures. The alumina starting material for the supports is commercially available of the commercially available alpha or gamma aluminas a superior carrier for the present reactions is formed by fluorination of the gamma alumina. The aluminas may be readily fluorinated in their commercially available form as granules or pellets with anhydrous HF diluted with nitrogen at temperatures ranging from about 200°–650° C. At low fluorination temperatures a mixture of alpha and gamma forms of $AlF_3$ is obtained. At high fluorination temperatures the alpha form of $AlF_3$ is obtained.

It is desirable according to the invention process that the weight percentage of cation in the Deacon catalyst during the oxychlorination reaction be in the range of 0.6-20, preferably 1-16 and, still preferably, 2-8, based on the total cation content of the Deacon catalyst and the stable, inert, metal salt carrier. For the purpose of determining the weight percentage of cation in the Deacon catalyst, the presence of cations in any additional metal salt promoters which are not themselves Deacon catalysts, shall be ignored. It is within the scope of this invention to charge a supported Deacon catalyst to the oxychlorination reaction in which the cation content of the Deacon catalyst exceeds the maximum 20 weight percent level defined herein and subsequently during the course of the oxychlorination reaction to permit the Deacon catalyst cation content to fall to within the desired limits. Use of a concentration of Deacon catalyst substantially in excess of the above-described 20 weight percent limitation on cation concentration, however, may result in an unstable catalyst with low activity and which creates corrosion problems. Such catalysts cannot be fluidized if desired and cannot be reused.

The reaction conditions in the oxychlorination zone will not differ from that found in conventional oxychlorination reactors wherein HCl is introduced as a separate reactant. For many reactions, temperatures between about 250° and about 500° C. are preferred, and contact times between about 0.1 and about 20 seconds are preferred. The amount of unhalogenated or underhalogenated hydrocarbon introduced will be sufficient for the molar ratio of hydrogens (plus double bonds times two) to HCl in the effluent to be between about 1/1 and 1/3. The amount of oxygen will be sufficient for the molar ratio of $O_2$ to C—H bonds (plus double bonds times two) to be between about 1:2 and 1:1.

SEPARATION AND RECYCLING

In preferred forms of the invention the effluent from the oxychlorination zone is separated into several fractions. Conveniently, since the effluent comprises compounds with boiling points spread over a range greater than 100° C, this separation can be accomplished by distillation. In practice, these separations generally occur by variation of both temperature and pressure to selectively condense each fraction, but for convenience the boiling points at constant, atmospheric pressures can be used for explanatory purposes. Application of these techniques to processes involving stills operating at different pressures involves techniques well known in the art.

Preferably, unreacted HF, HCl and $O_2$, as well as water by-product, are removed from the effluent gas before distillation. A caustic scrubber, dessication columns or both may be used. However, if the unreacted HF is to be recycled, it should be recovered upstream from the caustic scrubber. Its boiling point about 19.5° C would otherwise place it in the low boiling fraction with many of the products if ethane derivatives are involved.

Carbon dioxide resulting from combustion need not usually be separated from the effluent before distillation, since it is uncondensible at any of the temperatures at which separation of other components occurs. Recycled $CO_2$ may act as a diluent to avoid overheating and/or formation of explosive mixtures of hydrocarbon and $O_2$, and need be separated only after repeated recycling.

The organic components of the effluent from the oxychlorination zone are thus summarized in Table 1, showing their boiling points and characterization in the present processes.

Table 1

| Component | Boiling Point | Character |
|---|---|---|
| $CH_2=CHCl$ | −13.9° C | Underhalogenated |
| $C_2F_4Cl_2$ | 3.6 | Product |
| $C_2H_5Cl$ | 13.1 | Underhalogenated |
| $C_2F_3Cl_3$ | 47.6 | Product |
| $CH_3CHCl_2$ | 57.3 | Underhalogenated |
| $CHCl=CHCl$ | 60.1 | Underhalogenated |
| $CFCl=CCl_2$ | 71.0 | Underhalogenated |
| $CH_2ClCH_2Cl$ | 83.5 | Underhalogenated |
| $CHCl=CCl_2$ | 88.0 | Underhalogenated |
| $C_2F_2Cl_4$ | 92.8 | Perchlorinated* |
| $CHCl_2CH_2Cl$ | 113.5 | Underhalogenated |
| $C_2Cl_4$ | 120.8 | Perchlorinated** |

*Considered perchlorinated if more fluorinated products desired.
**Considered perchlorinated as a carrier for $C_2Cl_6$ or if chlorinated in situ or in side reaction.

It should be appreciated that two stills operating at between 47.6° and 57.3° C and between 88.0° and 92.8° C can separate the organics into a low boiling fraction containing both product components, a middle boiling component containing only underhalogenated hydrocarbons and a high boiling fraction containing mainly perchlorinated hydrocarbons as defined herein and $CHCl_2CH_2Cl$ which is sufficiently halogenated that it can safely be recycled to the fluorination zone without substantial increase in combustion.

The low boilers can be further distilled into the two products and the two underhalogenated hydrocarbons (as well as carbon dioxide). The entire middle boiling fraction and the low boiling $CH_2=CHCl$ and $C_2H_5Cl$ (and carbon dioxide) can be recycled onto the oxychlorination catalyst by reintroduction between the two catalyst zone.

The high boiling fraction is preferably recycled onto the fluorination catalyst by reintroduction at the upstream end. If more $C_2Cl_6$ is to be introduced, the high boiling fraction can be used to dissolve it. More $C_2Cl_6$ may be formed by chlorination of the high boiling fraction in a side reaction. Alternatively, $Cl_2$ may be mixed with $C_2Cl_4$ in the fluorination zone, but this is less preferred.

By using similar techniques separation into one or more fraction of products, "underhalogenated" compounds and "perchlorinated" hydrocarbons can be accomplished with one and three carbon systems as well. As with the two carbon system, multiple stills, side reactions such as chlorination and reintroduction of components of the effluent with the appropriate reactants may be employed.

EXAMPLES 1-3 PREPARATION OF CATALYSTS

Example 1

Preparation of Low Temperature Fluorinated $Al_2O_3$

A 1330 ml of 1492 g sample of γ-alumina (Harshaw Al-1404 T ⅛ inch, SA 180-200 m/g PV 0.42-0 51cc/g) was charged to a 3 inches 1D iron pipe to a depth of 25 inches. The reactor was placed in a sand bath and heated to 500° with $N_2$ flowing over the catalyst to dehydrate it. After cooling to 150° a mixture of 36g/h of HF and 38 1/h of $N_2$ was passed over the alumina. This caused a "hot spot" temperature of 250° to appear at the beginning of the bed. After 30 hours the "hot spot" had migrated to the end of the bed. The fluorination was temporarily stopped while the heating bath was raised to 400°. Fluorination was resumed using a mixture of 21g/h of HF and 38l/h of $N_2$. This caused a second "hot spot" of 420° to 426° which took 50 hours to migrate to the end of the bed. The fluorination was finished by feeding HF for 7 hours longer. The mole ratio of HF to $Al_2O_3$ was 7.7/1.0. X-ray diffraction pattern indicated the gamma form of $AlF_3$.

Example 2

Preparation of High Temperature Fluorinated $Al_2O_3$

A 1000 ml or 855 g sample of alumina tablets (Harshaw 0104 T ⅜ inch, SA 80–100 m²/g, PV 0-28-0.33 cc/g) was placed in a 2 inch 1D × 24 inch long Inconel Reactor and the reactor placed in a Procedyne Sand Bath held at 550° ± 5°. During the heating period, 25 g of water was evolved under a slow $N_2$ sweep of 10 l/h. HF, diluted with $N_2$, was then fed at 48–56 g/hr. A "hot spot" ranging from 554° to 642°, immediately developed and migrated slowly from the beginning of the catalyst bed to the end. Completion of fluorination was indicated by (1) lack of HF absorption (2) absence of hot-spot. After 17 hours fluorination appeared complete but HF flow was continued for 2 hours. The product was calculated to be 86.0% $AlF_3$ on the basis of a final weight of 1,336 g. X-ray diffraction pattern indicated the alpha form of $AlF_3$.

Example 3

Impregnation of Carrier with Deacon Catalyst

A 150 ml aqueous solution of $CuCl_2.2H_2O$ (53.0 g) and KCl (23.0 g) was added to 653 g of the high temperature fluorinated alumina of Example 2 in an evacuated flask (26 inches Hg). The slurry was shaken slightly to insure a uniform coating of the tablets. After drying overnight at 100°, in vacuo, the fluorinated alumina contained 6.0% $CuCl_2$/3,3% KCl.

Terminology

The following terms "%HCl Conversion", "%HF Conversion," "%$C_2H_6$ to $CO_2$" and "Contact Time" as used in Tables II and III and in Example 12 are defined as follows:

% HCl Conversion $$\frac{(\text{moles HF consumed} - \text{moles Cl}^- \text{ found})}{\text{moles HF consumed}} \times 100$$

moles HF consumed = moles HF charged − moles HF in effluent

% HF Conversion $$\frac{\text{moles HF consumed}}{\text{moles HF charged}} \times 100$$

% $C_2H_6$ [or other hydrocarbon feed] to $CO_2$ $$\frac{\text{moles CO}_2 \times \frac{1}{2}}{\text{moles C}_2\text{H}_6 \text{ [or other hydrocarbon feed]}} \times 100 \text{ (2 moles CO}_2 \text{ per mole C}_2\text{H}_6\text{)}$$

Contact Time $$\text{Seconds} = \frac{\text{Catalyst Vol. (ml)} \times 273° \times 3600 \text{ sec}}{22,400 \text{ ml} \times \text{bath temp (K)} \times \text{moles (reactants)}}$$

Examples 4–8

Ethane as Unhalogenated Hydrocarbon Reactant

A 1½ × 22 inch long Inconel reactor was charged with 225 ml (343 g) of low temperature fluorinated alumina at the upstream end. This was followed by 225 ml (307 g) of high temperature fluorinated alumina coated with 2.0% $CuCl_2$/1.1% KCl to form two contiguous zones. The total catalyst bed length was 14 inches.

The reactor was placed vertically in a heated fluidized sand bath and the reactants were fed. The following reactant flow rates were used giving a ten second contact time at a sand bath temperature of 400° C:

| $C_2Cl_6$ | 0.23 m/h | $C_2H_6$ | 0.23 m/h |
|---|---|---|---|
| $C_2Cl_4$ | 0.99 | $O_2$ | 0.57 |
| HF | 0.925 | | |

Solid $C_2Cl_6$ was conveniently introduced as a 25% solution in $C_2Cl_4$. M.R. $C_2Cl_6/C_2Cl_4 = 1.0/4.3$.

These ratios of reactants are based upon the following predicted stoichiometry directed to $C_2F_4Cl_2$.

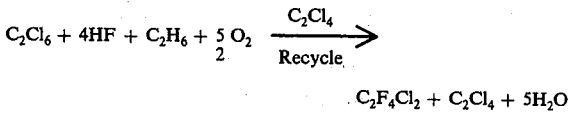

$$C_2Cl_6 + 4HF + C_2H_6 + 5O_2 \xrightarrow[\text{Recycle}]{C_2Cl_4} C_2F_4Cl_2 + C_2Cl_4 + 5H_2O$$

All the reactants were preheated by the sand bath as they entered through the bottom of the reactor. The $C_2H_6$, however, entered through a separate inlet tube which extended half-way up the catalyst bed to the oxychlorination zone. After about one hour the temperature profile of the catalyst stabilized. There were two temperature maxima or "hot spots" observed. One was at the beginning of the bed (406°) and the other (437°) at the middle of the bed. The experiment lasted about 3 hours during which time product samples were obtained for analysis.

The results of four such runs are displayed in Table II. In each case the non-halogenated hydrocarbon was ethane. Examples 5 and 6 show the effect of a different mode of introducing $C_2H_6$, with Example 5 being as preferred in the present invention. Examples 6 and 7 show the effect of different contact times and stoichiometry.

Table II

| OXYCHLOROFLUORINATION OF ETHANE | | | | |
|---|---|---|---|---|
| Example | 4 | 5 | 6 | 7 |
| $C_2H_6$ Feed Pt. | Upstream End | Mid Point | Mid Point | Mid Point |
| Reactants | | | | |
| $C_2Cl_6$ m/h | 0.14 | 0.14 | 0.11 | 0.23 |
| $C_2Cl_4$ | 0.60 | 0.62 | 0.46 | 0.99 |
| HF | 0.41 | 0.39 | 0.45 | 0.93 |
| $C_2H_6$ | 0.105 | 0.105 | 0.115 | 0.23 |
| $O_2$ | 0.25 | 0.25 | 0.29 | 0.57 |
| Reaction Temp ° C | 400 | 400 | 400 | 400 |
| "Hot Spot" 0"/8" | 400/423 | 400/428 | 405/424 | 406/437 |
| Contact Time (sec) | 20 | 20 | 20 | 10 |
| %HF Conversion | 21 | 73 | 82 | 75 |
| %HCl Conversion | 78 | 99 | 92 | 82 |
| %$C_2H_6$ to $CO_2$ | 43 | 24 | 23 | 15 |
| Running time (hr.) | 2.5 | 3.0 | 3.3 | 1.5 |

The Composition* of the organic components in the effluent tube of Example 7 was determined by Gas Chromatography analysis as follows:

| $C_2H_6$ | 1.3 mol % | $CH_2ClCH_2Cl$ | 7.8 mol % |
|---|---|---|---|
| $C_2H_4$ | 2.9 | $CHCl=CCl_2$ | 4.0 |
| $CO_2$ | 3.3 | $CHCl_2CH_2Cl$ | 4.4 |
| $CH_2=CHCl$ | 4.0 | $CCl_2=CCl_2$ | 5.8 |
| $C_2H_5Cl$ | 8.4 | $C_2F_4Cl_2$ | 16.4 |
| $CHCl=CHCl$ | 3.3 | $C_2F_3Cl_3$ | 19.5 |
| $CH_3CHCl_2$ | 3.8 | $C_2F_2Cl_4$ | 5.1 |
| | | $CFCl=CCl_2$ | 10.0 |

*Values were normalized after excluding $CCl_2=CCl_2$ solvent.

EXAMPLE 8

The effluent of Example 7 is freed of $H_2O$, HCl and HF by passage through a water bath, a caustic scrubber and a dessicant column. The remaining effluent is then condensed in three stills at 90° C, 55° C and −20° C. The high boiling condensate from the first still is recycled, with additional $C_2Cl_6$ to the upstream end of the reactor. The middle boiling condensate of the second still is recycled into the separate inlet tube halfway up the catalyst bed. The low boiling condensate from the third still is further processed in stills operating at −10° C, 10° C and 30° C into the two products and the two low boiling underhalogenated hydrocarbons $CH_2$=CHCl and $C_2H_5Cl$. The underhalogenated hydrocarbons are recycled into the separate inlet.

Examples 9–11

Other $C_2$ Underhalogenated Reactants

The following processes were run, using the apparatus of Examples 1–7 and the reactant flow ratio shown in Table III. Note that the "hydrocarbon feed" in Example 9 is ethylene and in Examples 10 and 11 the underhalogenated chlorocarbons $C_2H_5Cl$ and $C_2H_4Cl_2$. The reactant ratio are based upon the following predicted stoichiometries:

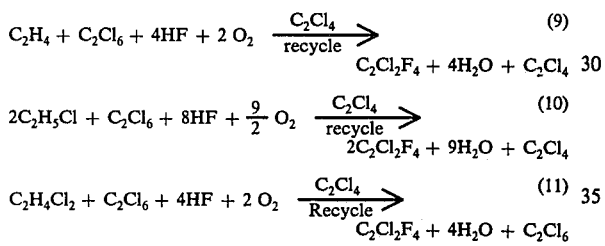

$$C_2H_4 + C_2Cl_6 + 4HF + 2 O_2 \xrightarrow[\text{recycle}]{C_2Cl_4} C_2Cl_2F_4 + 4H_2O + C_2Cl_4 \quad (9)$$

$$2C_2H_5Cl + C_2Cl_6 + 8HF + \tfrac{9}{2} O_2 \xrightarrow[\text{recycle}]{C_2Cl_4} 2C_2Cl_2F_4 + 9H_2O + C_2Cl_4 \quad (10)$$

$$C_2H_4Cl_2 + C_2Cl_6 + 4HF + 2 O_2 \xrightarrow[\text{Recycle}]{C_2Cl_4} C_2Cl_2F_4 + 4H_2O + C_2Cl_6 \quad (11)$$

Table III
OXYCHLOROFLUORINATION EXPERIMENTS AT 400° C/10 SECOND CONTACT TIME

| Example | 9 | 10 | 11 |
|---|---|---|---|
| Hydrocarbon Reactant Feed m/h | $C_2H_4$ | $C_2H_5Cl$ | $C_2H_4Cl_2$ |
| Hydrocarbon | 0.24 | 0.24 | 0.24 |
| $C_2Cl_6$ | .24 | .23 | .23 |
| $C_2Cl_4$ | .98 | .99 | 1.01 |
| HF | .95 | .96 | .95 |
| $O_2$ | .48 | .53 | .48 |
| "Hot Spot" 0"/8" | 406/431 | 406/432 | 404/423 |
| %HF Con. | 75 | 69 | 64 |
| %HCl Con. | 71 | 75 | 53 |
| % Hydrocarbon feed to $CO_2$ | 12 | 8 | 6 |

Example 12

Methane as Hydrocarbon Feed

This example illustrates the use of methane as the hydrocarbon feed.

A 1 ½ inch × 22 inch long Inconel reactor was charged with 130 ml of the Catalyst of Example 1 and 320 ml of the Catalyst of Example 2 which was impregnated with 2.0% $CuCl_2$ and 1.1% KCl. A mixture of $Cl_2/HF/O_2/CCl_4/CH_4$ at a mole ratio of 1.25/1.50/1.38/1.50/1.00 was passed over the catalyst at 400° and 10 second contact time. The respective conversions of $Cl_2$, HF and HCl were 98, 90 and 42%. Fourteen percent of the $CH_4$ was converted to $CO_2$. The use of the Catalyst of Example 1 which is very active for fluorination produced a significantly higher HF conversion than if the catalyst was entirely the catalyst of Example 2 or 3.

Example 13

Undesired Side Chlorination Reaction

The effect of the undesired side reaction sequences such as the following were tested:

$$C_2Cl_6 \rightleftharpoons C_2Cl_4 + Cl_2$$

$$C_2H_6 + Cl_2 \rightarrow C_2H_5Cl + HCl$$

$C_2Cl_6$ at 0.14 m/h, $C_2Cl_4$ at 0.58 m/h, $C_2H_6$ at 0.10 m/h and $N_2$ were all fed into the upstream end of the reaction device of Examples 4–11 at 400° C with a "Contact Time" of 20 seconds. The effluent was analyzed by Gas Chromatography and showed the presence of $C_2H_4$, $C_2H_6$, $CH_2$=CHCl, CHCl=CHCl (cis/trans), $CH_2ClCH_2Cl$, $C_2H_5Cl$ and CHCl=$CCl_2$. Wet analysis of effluent for $Cl^-$ showed 0.16 m/h.

These side reactions are to a large extent avoided in the present process because the $C_2Cl_6$ is fluorinated before coming into contact with $C_2H_6$ and the like.

We claim:

1. A process for producing fluorocarbons having 1 to 3 carbons comprising the steps of:
   (a) reacting chlorinated hydrocarbons having 1 to 3 carbons selected from the group consisting of perchlorinated hydrocarbons, highly chlorinated hydrocarbons and mixtures thereof with HF in the presence of a fluorination catalyst to produce an effluent containing fluorocarbon products and HCl; and
   (b) reacting compounds having 1 to 3 carbons selected from the group consisting of underhalogenated hydrocarbons, non-halogenated hydrocarbons and mixtures thereof with $O_2$ and said effluent in the presence of an oxychlorination catalyst inert to HF to produce a second effluent containing fluorocarbon products and highly chlorinated and perchlorinated hydrocarbons.

2. A method as claimed in claim 1 wherein said fluorination catalyst is selected from the group consisting of the gamma fluoride of aluminum, the fluorides of chromium, nickel, cobalt, thorium, zirconium and antimony and the partially fluorinated oxides of aluminum and chronium.

3. A method as claimed in claim 1 wherein said fluorination catalyst is selected from the group consisting of gamma aluminum fluoride, chromium fluoride and partially fluorinated oxides of aluminum and chromium.

4. A method as claimed in claim 1 wherein said oxychlorination catalyst comprises particles of an inert base coated with a transition metal halide or oxide.

5. A method as claimed in claim 4 wherein said oxychlorination catalyst further includes an alkali or alkaline earth halide promoter.

6. A method as claimed in claim 1 wherein said perchlorinated hydrocarbon is $C_2Cl_6$, and said underhalogenated and non-halogenated hydrocarbons are selected from the groups consisting of $C_2H_6$, $C_2H_5Cl$, $C_2H_4$, $C_2H_3Cl$ and mixtures thereof.

7. A method as claimed in claim 1 wherein an external chlorine source selected from $Cl_2$ or HCl is fed onto the oxychlorination catalyst.

8. A method as claimed in claim 1 wherein an external chlorine source selected from the group consisting of $Cl_2$ and HCl is reacted with the effluent from the oxychlorination catalyst and perchlorinated hydrocarbons are recovered.

9. A method as claimed in claim 1 further including removing HCl, $H_2O$, HF, combustion products and $O_2$ from the second effluent and separating the remaining effluent into at least one perchlorinated hydrocarbon fraction, at least one under halogenated hydrocarbon fraction and at least one fluorocarbon product fraction; and recycling the perchlorinated hydrocarbon fraction onto the fluorination catalyst.

10. A method as claimed in claim 9 wherein said perchlorinated hydrocarbon fraction contains $C_2Cl_4$ and said method further includes reacting said perchlorinated hydrocarbon fraction with $Cl_2$ to convert $C_2Cl_4$ to $C_2Cl_6$ before reintroducing said perchlorinated hydrocarbon fraction onto said fluorination catalyst.

11. A method as claimed in claim 9 wherein said underhalogenation hydrocarbon fraction is introduced onto said oxychlorinated catalyst.

12. A method as claimed in claim 1 wherein said oxygen is fed onto said fluorination catalyst.

* * * * *

UNITED STATES PATENT AND TRADEMARK OFFICE
CERTIFICATE OF CORRECTION

PATENT NO. : 4,088,704
DATED : May 9, 1978
INVENTOR(S) : Henry R. Nychka and Richard E. Eibeck It is certified that error appears in the above-identified patent and that said Letters Patent are hereby corrected as shown below:

Column 6, line 56, "available of" should read --available. Of--

Column 14, line 8, "underhalogenation" should read

--underhalogenated--

Column 14, line 9, "oxychlorinated" should read

--oxychlorination--

Signed and Sealed this

Seventeenth Day of July 1979

[SEAL]

Attest:

Attesting Officer

LUTRELLE F. PARKER
Acting Commissioner of Patents and Trademarks